United States Patent
Baron et al.

(10) Patent No.: US 11,633,229 B2
(45) Date of Patent: Apr. 25, 2023

(54) 3D ELECTRICAL ACTIVITY REPRESENTATION

(71) Applicant: BIOSENSE WEBSTER (ISRAEL) LTD., Yokneam (IL)

(72) Inventors: Oded Baron, Haifa (IL); Stanislav Goldberg, Haifa (IL); Shmuel Auerbach, Kerem Maharal (IL)

(73) Assignee: Biosense Webster (Israel) Ltd., Yokeam (IL)

( * ) Notice: Subject to any disclaimer, the term of this patent is extended or adjusted under 35 U.S.C. 154(b) by 506 days.

(21) Appl. No.: 16/594,668

(22) Filed: Oct. 7, 2019

(65) Prior Publication Data
US 2021/0100612 A1 Apr. 8, 2021

(51) Int. Cl.
A61B 18/14 (2006.01)
A61B 5/06 (2006.01)
A61B 6/00 (2006.01)
G06F 3/04815 (2022.01)
G06T 7/00 (2017.01)

(52) U.S. Cl.
CPC .......... *A61B 18/1492* (2013.01); *A61B 5/061* (2013.01); *A61B 6/466* (2013.01); *G06F 3/04815* (2013.01); *G06T 7/0012* (2013.01)

(58) Field of Classification Search
CPC .............................. A61B 18/1492; A61B 5/061
See application file for complete search history.

(56) References Cited

U.S. PATENT DOCUMENTS

| | | |
|---|---|---|
| 5,391,199 A | 2/1995 | Ben Haim |
| 6,239,724 B1 | 5/2001 | Doron |
| 6,332,089 B1 | 12/2001 | Acker |
| 6,484,118 B1 | 11/2002 | Govari |
| 6,618,612 B1 | 9/2003 | Acker |
| 6,690,963 B2 | 2/2004 | Ben Haim |
| 7,756,576 B2 | 7/2010 | Levin |
| 7,848,787 B2 | 12/2010 | Osadchy |
| 7,869,865 B2 | 1/2011 | Govari |
| 2002/0006455 A1 | 1/2002 | Levine |

(Continued)

FOREIGN PATENT DOCUMENTS

| | | |
|---|---|---|
| CN | 110198680 A | 9/2019 |
| EP | 3453323 A1 | 3/2019 |

(Continued)

*Primary Examiner* — Yi Yang (57) ABSTRACT

In one embodiment, a medical system includes a catheter including electrodes, and configured to be inserted into a chamber of a heart and maneuvered among sampling sites to sample electrical activity, a display, and processing circuitry to receive signals provided by the catheter, and compute, for each sampling site, a sampling position of the catheter and respective electrode positions of the catheter electrodes, render to the display a 3D representation of the chamber including respective sampling-site markers indicating the computed sampling position of the catheter at respective ones of the sampling sites, receive a user input selecting one sampling-site marker, and update the 3D representation to include electrode markers indicating the respective electrode positions of the respective catheter electrodes while the catheter was sampling the electrical activity of the tissue at the sampling site corresponding to the selected sampling-site marker.

21 Claims, 9 Drawing Sheets

(56) References Cited

U.S. PATENT DOCUMENTS

| | | | |
|---|---|---|---|
| 2002/0065455 A1 | 5/2002 | Ben Haim | |
| 2003/0120150 A1 | 6/2003 | Govari | |
| 2003/0228639 A1* | 12/2003 | Wright | G01N 33/57434 |
| | | | 702/19 |
| 2004/0068178 A1 | 4/2004 | Govari | |
| 2005/0228252 A1 | 10/2005 | Neason | |
| 2007/0276226 A1 | 11/2007 | Tal | |
| 2009/0262979 A1 | 10/2009 | Markowitz | |
| 2013/0158545 A1 | 6/2013 | Govari | |
| 2014/0098099 A1* | 4/2014 | Welford | G06T 19/20 |
| | | | 345/427 |
| 2016/0022375 A1 | 1/2016 | Blake | |
| 2016/0242666 A1* | 8/2016 | Pujar | G16H 40/63 |
| 2017/0027465 A1 | 2/2017 | Blauer | |
| 2017/0105678 A1* | 4/2017 | Xue | A61B 5/25 |
| 2017/0202470 A1 | 7/2017 | Urman | |
| 2017/0202515 A1 | 7/2017 | Zrihem | |
| 2018/0160978 A1* | 6/2018 | Cohen | G06T 7/0012 |
| 2019/0076045 A1* | 3/2019 | Katz | G16H 50/50 |

FOREIGN PATENT DOCUMENTS

| | | |
|---|---|---|
| RU | 2013158764 A | 7/2015 |
| WO | WO1996005768 A1 | 2/1996 |
| WO | WO2019105986 A1 | 6/2019 |

\* cited by examiner

3D ELECTRICAL ACTIVITY REPRESENTATION

FIELD OF THE INVENTION

The present invention relates to medical systems, and in particular, but not exclusively to, catheter-based systems.

BACKGROUND

A wide range of medical procedures involve placing probes, such as catheters, within a patient's body. Location sensing systems have been developed for tracking such probes. Magnetic location sensing is one of the methods known in the art. In magnetic location sensing, magnetic field generators are typically placed at known locations external to the patient. A magnetic field sensor within the distal end of the probe generates electrical signals in response to these magnetic fields, which are processed to determine the coordinate locations of the distal end of the probe. These methods and systems are described in U.S. Pat. Nos. 5,391,199, 6,690,963, 6,484,118, 6,239,724, 6,618,612 and 6,332,089, in PCT International Publication No. WO 1996/005768, and in U.S. Patent Application Publications Nos. 2002/006455 and 2003/0120150 and 2004/0068178. Locations may also be tracked using impedance or current based systems.

One medical procedure in which these types of probes or catheters have proved extremely useful is in the treatment of cardiac arrhythmias. Cardiac arrhythmias and atrial fibrillation in particular, persist as common and dangerous medical ailments, especially in the aging population.

Diagnosis and treatment of cardiac arrhythmias include mapping the electrical properties of heart tissue, especially the endocardium and the heart volume, and selectively ablating cardiac tissue by application of energy. Such ablation can cease or modify the propagation of unwanted electrical signals from one portion of the heart to another. The ablation process destroys the unwanted electrical pathways by formation of non-conducting lesions. Various energy delivery modalities have been disclosed for forming lesions, and include use of microwave, laser and more commonly, radiofrequency energies to create conduction blocks along the cardiac tissue wall. In a two-step procedure, mapping followed by ablation, electrical activity at points within the heart is typically sensed and measured by advancing a catheter containing one or more electrical sensors into the heart, and acquiring data at a multiplicity of points. These data are then utilized to select the endocardial target areas at which the ablation is to be performed.

Electrode catheters have been in common use in medical practice for many years. They are used to stimulate and map electrical activity in the heart and to ablate sites of aberrant electrical activity. In use, the electrode catheter is inserted into a major vein or artery, e.g., femoral artery, and then guided into the chamber of the heart of concern. A typical ablation procedure involves the insertion of a catheter having a one or more electrodes at its distal end into a heart chamber. A reference electrode may be provided, generally taped to the skin of the patient or by means of a second catheter that is positioned in or near the heart. RF (radio frequency) current is applied to the tip electrode(s) of the ablating catheter, and current flows through the media that surrounds it, i.e., blood and tissue, toward the reference electrode. The distribution of current depends on the amount of electrode surface in contact with the tissue as compared to blood, which has a higher conductivity than the tissue. Heating of the tissue occurs due to its electrical resistance. The tissue is heated sufficiently to cause cellular destruction in the cardiac tissue resulting in the formation of a lesion within the cardiac tissue which is electrically non-conductive.

US Patent Publication 2017/0202470 to Urman, et al., describes a system and method of identifying focal sources. The method can comprise detecting, via sensors, electrocardiogram (ECG) signals over time, each ECG signal detected via one of the sensors having a location in a heart and indicating electrical activity of the heart, each signal comprising at least an R wave and an S wave; creating an R-S map comprising an R-to-S ratio for each of the ECG signals, the R-to-S ratio comprising a ratio of absolute magnitude of the R wave to absolute magnitude of the S wave; identifying, for each of the ECG signals, local activation times (LATs); and correlating the R-to-S ratios for the ECG signals on the R-S map and the identified LATs and using the correlation to identify the focal sources.

US Patent Publication 2017/0202515 to Ben Zrihem, et al., describes a method of atrial rotational activity pattern (RAP) source detection which includes detecting, via a plurality of sensors, electro-cardiogram (ECG) signals over time, each ECG signal detected via one of the plurality of sensors and indicating electrical activity of a heart. The method also includes determining, for each of the plurality of ECG signals, one or more local activation times (LATs) each indicating a time of activation of a corresponding ECG signal. The method further includes detecting whether one or more RAP source areas of activation in the heart is indicated based on the detected ECG signals and the one or more local LATs. Mapping information of the detected RAP source areas of activation in the heart is also generated for providing one or more maps.

US Patent Publication 2005/0228252 to Neason describes a system that comprises one or more probes configured to be positioned inside a heart of a patient, a processor communicatively coupled to the one or more probes, a display communicatively coupled to the processor, and image processing tools which are used by the processor to manipulate the image. The processor being used to process electrical information pertaining to the heart. The electrical information is sensed using the one or more probes. The display is used to display an image of the heart.

US Patent Publication 2016/0022375 to Blake, et al., describes a system for determining cardiac targets. The system may include at least one processing device configured to carry out instructions to receive cardiac imaging data, segment the cardiac imaging data to identify at least two types of cardiac tissue, generate a cardiac model based on the identified tissue, simulate cardiac activity based on the generated cardiac model, and identify at least one cardiac target based on the simulation. A cardiac therapy system may be utilized to provide feedback to a user in order to guide a cardiac treatment device to a cardiac target.

US Patent Publication 2013/0158545 to Govari, et al., describes methods and systems to treat abnormal cardiac electrical activity employing a probe having first and second ablation electrodes disposed on a distal portion of the probe and a sensing electrode disposed between the first and second ablation electrodes, bringing the probe into contact with cardiac tissue, and applying energy through the first and second ablation electrodes to ablate target tissue along an ablation path, monitoring cardiac electrical activity using the sensing electrode to detect the cardiac electrical activity. After making an observation that the cardiac electrical activity is no longer detectable by the sensing electrode, energy application is terminated.

US Patent Publication 2007/0276226 to Tal describes using specialized cardiac catheters for image acquisition, features of the heart being readily identifiable on an ultrasound image, based on a previously generated electrical activation map of the heart. The electrical activation map is automatically registered with the ultrasound image using information obtained from position sensors in the catheters. Features identifiable on the electrical activation map, presented as points, tags, design lines, and textual identification, are projected into the plane of the ultrasound fan and overlaid on the ultrasound image, thereby clarifying the features that are visible on the latter.

SUMMARY

There is provided in accordance with an embodiment of the present invention, a medical system, including a catheter including a distal portion and catheter electrodes disposed at respective locations on the distal portion, and configured to be inserted into a chamber of a heart of a living subject and maneuvered among multiple sampling sites to sample electrical activity of the chamber using respective ones of the catheter electrodes at each of the sampling sites, a display, and processing circuitry configured to receive signals provided by the catheter, and in response to the signals, compute, for each of the sampling sites, a sampling position of the catheter and respective electrode positions of the respective ones of the catheter electrodes, render to the display a three-dimensional (3D) representation of the chamber including respective sampling-site markers indicating the computed sampling position of the catheter at respective ones of the sampling sites, receive a user input selecting one of the sampling-site markers, and update the rendered 3D representation, responsively to the received user input, to include electrode markers indicating the respective electrode positions of the respective catheter electrodes while the catheter was sampling the electrical activity of the tissue at a respective one of the sampling sites corresponding to the selected sampling-site marker.

Further in accordance with an embodiment of the present invention, the processing circuitry is configured to compute, for each of the sampling sites, the sampling position and the electrode positions as average positions of the catheter and the catheter electrodes, respectively, averaged over a sampling time.

Still further in accordance with an embodiment of the present invention, the processing circuitry is configured to update the rendered 3D representation to highlight the selected sampling-site marker.

Additionally in accordance with an embodiment of the present invention, the processing circuitry is configured to identify electrical activity of the tissue sensed by respective ones of the catheter electrodes sampled at respective sampling sites, and update the rendered 3D representation, responsively to the received user input, to include the electrode markers with at least one of the electrode markers having a different presentation type than other ones of the electrode markers responsively to the identified electrical activity of the tissue sensed by at least one respective one of catheter electrodes.

Moreover, in accordance with an embodiment of the present invention, the identified electrical activity is electrical activity below a threshold activity level.

Further in accordance with an embodiment of the present invention, the identified electrical activity is focal activity.

Still further in accordance with an embodiment of the present invention, the identified electrical activity is rotational activity.

Additionally, in accordance with an embodiment of the present invention, the different presentation type includes using a larger electrode marker compared with the other electrode markers.

Moreover, in accordance with an embodiment of the present invention, the different presentation type includes using a different color electrode marker compared with the other electrode markers.

Further in accordance with an embodiment of the present invention the processing circuitry is configured to format the at least one electrode marker an intensity of the identified electrical activity of the tissue sensed by the at least one respective one of the catheter electrodes.

There is also provided in accordance with another embodiment of the present invention, a medical method, including receiving signals provided by a catheter, the catheter including a distal portion and catheter electrodes disposed at respective locations on the distal portion, and configured to be inserted into a chamber of a heart of a living subject and maneuvered among multiple sampling sites to sample electrical activity of tissue of the chamber using respective ones of the catheter electrodes at each of the sampling sites, in response to the signals, computing, for each of the sampling sites, a sampling position of the catheter and respective electrode positions of the respective ones of the catheter electrodes, rendering to a display a three-dimensional (3D) representation of the chamber including respective sampling-site markers indicating the computed sampling position of the catheter at respective ones of the sampling sites, receiving a user input selecting one of the sampling-site markers, and updating the rendered 3D representation, responsively to the received user input, to include electrode markers indicating the respective electrode positions of the respective catheter electrodes while the catheter was sampling the electrical activity of the tissue at a respective one of the sampling sites corresponding to the selected sampling-site marker.

Still further in accordance with an embodiment of the present invention, the computing includes computing, for each of the sampling sites, the sampling position and the electrode positions as average positions of the catheter and the catheter electrodes, respectively, averaged over a sampling time.

Additionally, in accordance with an embodiment of the present invention, the updating includes updating the rendered 3D representation to highlight the selected sampling-site marker.

Moreover in accordance with an embodiment of the present invention, the method includes identifying electrical activity of the tissue sensed by respective ones of the catheter electrodes sampled at the respective sampling sites, wherein the updating includes updating the rendered 3D representation, responsively to the received user input, to include the electrode markers with at least one of the electrode markers having a different presentation type than other ones of the electrode markers responsively to the identified electrical activity of the tissue sensed by at least one respective one of the catheter electrodes.

Further in accordance with an embodiment of the present invention, the identified electrical activity is electrical activity below a threshold activity level.

Still further in accordance with an embodiment of the present invention, the identified electrical activity is focal activity.

Additionally, in accordance with an embodiment of the present invention, the identified electrical activity is rotational activity.

Moreover, in accordance with an embodiment of the present invention, the different presentation type includes using a larger electrode marker compared with the other electrode markers.

Further in accordance with an embodiment of the present invention, the different presentation type includes using a different color electrode marker compared with the other electrode markers.

Still further in accordance with an embodiment of the present invention, the method includes formatting the at least one electrode marker an intensity of the identified electrical activity of the tissue sensed by the at least one respective one of the catheter electrodes.

There is also provided in accordance with still another embodiment of the present invention, a software product, including a non-transient computer-readable medium in which program instructions are stored, which instructions, when read by a central processing unit (CPU), cause the CPU to receive signals provided by a catheter, the catheter including a distal portion and catheter electrodes disposed at respective locations on the distal portion, and configured to be inserted into a chamber of a heart of a living subject and maneuvered among multiple sampling sites to sample electrical activity of tissue of the chamber using respective ones of the catheter electrodes at each of the sampling sites, compute, in response to the signals, for each of the sampling sites, a sampling position of the catheter and respective electrode positions of the respective ones of the catheter electrodes, render to a display a three-dimensional (3D) representation of the chamber including respective sampling-site markers indicating the computed sampling position of the catheter at respective ones of the sampling sites, receive a user input selecting one of the sampling-site markers, and update the rendered 3D representation, responsively to the received user input, to include electrode markers indicating the respective electrode positions of the respective catheter electrodes while the catheter was sampling the electrical activity of the tissue at a respective one of the sampling sites corresponding to the selected sampling-site marker.

BRIEF DESCRIPTION OF THE DRAWINGS

The present invention will be understood from the following detailed description, taken in conjunction with the drawings in which.

DESCRIPTION OF EXAMPLE EMBODIMENTS

Overview

Presentation of electrical activity and sampling locations sampled by complex multi spline catheters (e.g., a PENTARAY® catheter of Biosense Webster, Inc., Irvine, Calif. USA, or a basket catheter) or multi-electrodes on linear catheters in a way which is intuitive for the physician is challenging due to the geometric distribution of the electrodes. Presentation is further complicated when continuous electrical acquisition of data over an extended time period (e.g., up to around 30 seconds) is used, as opposed to regular electro-anatomical (EA) points which may include only 2.5 seconds of signal data. When data is acquired over an extended period, some of the data may or may not be useful due to instability of the catheter during the sampling period.

Embodiments of the present invention, solve the above problems by providing an intuitive three-dimensional (3D) representation of the heart chamber including respective sampling-site markers indicating various sampling positions of the catheter at respective sampling sites. Upon selection of a sampling-site marker, the 3D representation is updated to show electrode markers indicating respective electrode positions of respective catheter electrodes while the catheter was sampling the electrical activity of tissue of the chamber at the sampling site corresponding to the selected sampling-site marker.

In disclosed embodiments, a catheter, including a distal portion and catheter electrodes placed at respective locations on the distal portion, is inserted into a chamber of a heart of a living subject and maneuvered among multiple sampling sites to sample electrical activity of tissue of the chamber using respective catheter electrodes at each sampling site. The distal portion of the catheter may include any suitable distal end assembly, such as a basket or balloon assembly or multiple splines connected to a distal end of a shaft of the catheter.

Processing circuitry receives signals provided by the catheter, and in response to the signals, computes, for each sampling site, a sampling position of the catheter and respective electrode positions. The sampling position of the catheter may be any suitable position of the catheter, for example, a distal end of the shaft of the catheter, or a position of a position sensor on the shaft, or an average position of the electrodes at the sampling site. The signals may be provided by the electrodes or other position sensor(s) or transducer(s) of the catheter. Signals may be received by the processing circuitry via a cable or wirelessly from the catheter, or from body surface patches which receive signals emitted by the catheter. In some embodiments, the processing circuitry computes, for each sampling site, the sampling position and the electrode positions as average positions of the catheter and the catheter electrodes, respectively, averaged over the sampling time at that sampling site.

The processing circuitry identifies electrical activity of the tissue sensed by respective catheter electrodes sampled at respective sampling sites based on the received signals. Identifying electrical activity may include identifying regions of interest such as focal activity or rotational activity, by way of example only. Focal activity may be indicated by a repetitive activation pattern that demonstrates early consecutive QS morphology. US Patent Publication 2017/0202470 of Urman et al., describes a system and method of identifying focal sources. Any suitable method to identify focal sources may be used. Rotational activity may be indicated by a repetitive activation pattern which demonstrates rotation activity. US Patent Publication 2017/0202515 of Ben Zrihem et al., describes a method of atrial rotational activity pattern (RAP) source detection which includes detecting, via a plurality of sensors, electro-cardiogram (ECG) signals over time, each ECG signal detected via one of the plurality of sensors and indicating electrical activity of a heart. Any suitable method to identify rotational activity may be used.

The processing circuitry renders to a display a 3D representation of the chamber including respective sampling-site markers (e.g., circles or squares or any suitable shape or symbol) indicating the computed sampling position of the catheter at respective sampling sites.

Upon receiving a user input selecting one of the sampling-site markers, the processing circuitry updates the rendered 3D representation to include electrode markers (e.g., circles or squares or any suitable shape or symbol) indicating the respective electrode positions of the respective catheter electrodes while the catheter was sampling the electrical activity of the tissue at the sampling sites corresponding to the selected sampling-site marker. In some embodiments, the processing circuitry updates the rendered 3D representation to highlight the selected sampling-site marker, for example, by using a brighter marker and/or placing a ring around the marker.

In some embodiments, a presentation type (e.g., shape and/or format) of the electrode markers is updated according to the identified electrical activity of the tissue sensed by the respective electrodes. The processing circuitry updates the rendered 3D representation, responsively to the received user input, to include the electrode markers with at least one electrode marker having a different presentation type than other electrode markers responsively to the identified electrical activity of the tissue sensed by respective catheter electrodes. The identified electrical activity which triggers the different presentation type may include: electrical activity below a threshold activity level, focal activity, and/or rotational activity. The different presentation type may include using a larger electrode marker compared with the other electrode markers, and/or a different color electrode marker compared with the other electrode markers, and/or different shapes, shading, patterns and/or brightness, by way of example.

In some embodiments, the processing circuitry formats the electrode marker(s) according to an intensity of the identified electrical activity of the tissue sensed by the respective catheter electrode(s). The format may include a color, shading, pattern, and/or brightness, by way of example, to indicate the intensity of the identified electrical activity.

System Description

Figure 1:
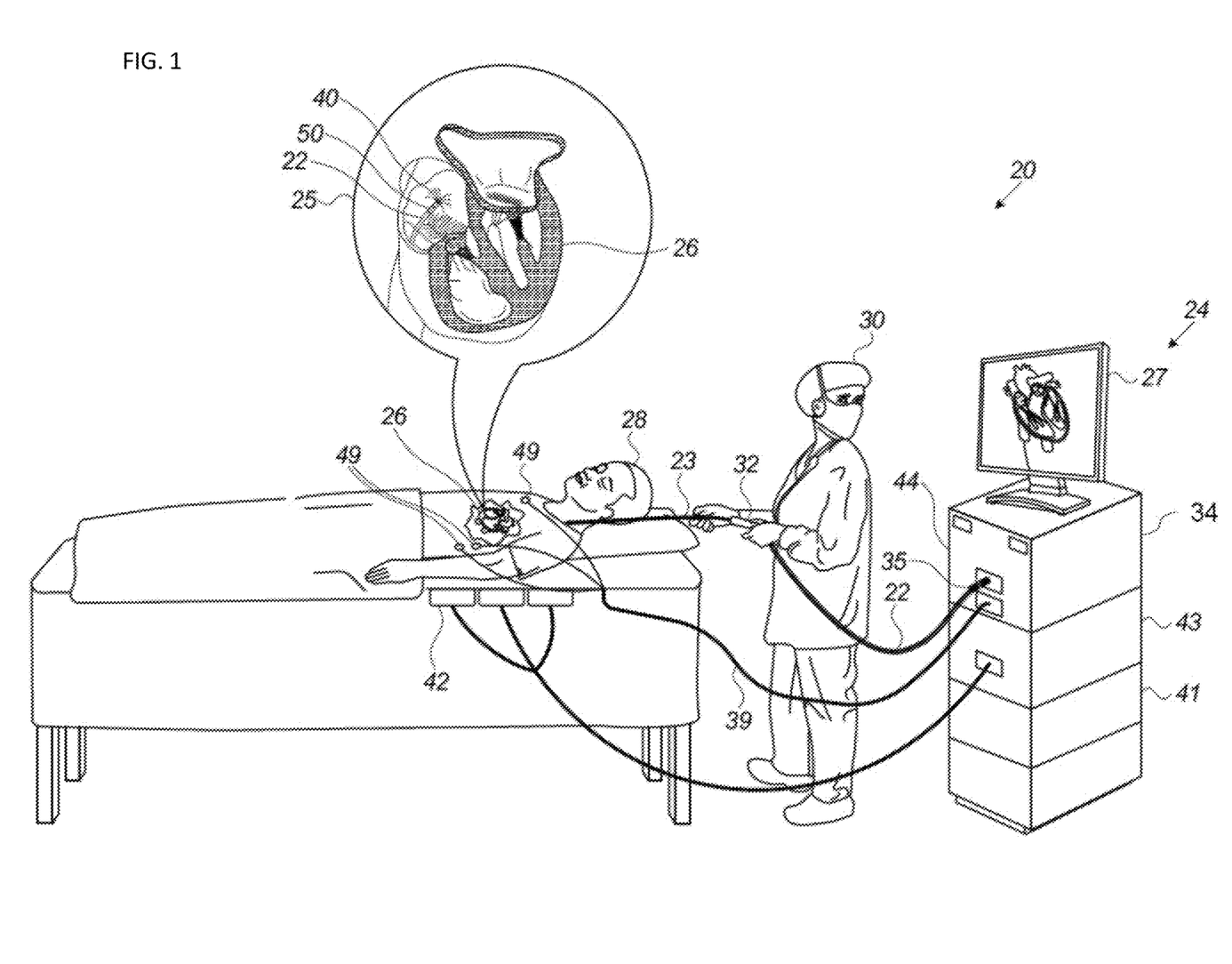
FIG. 1 is a schematic view of a medical procedure system constructed and operative in accordance with an embodiment of the present invention.
Figure 2:
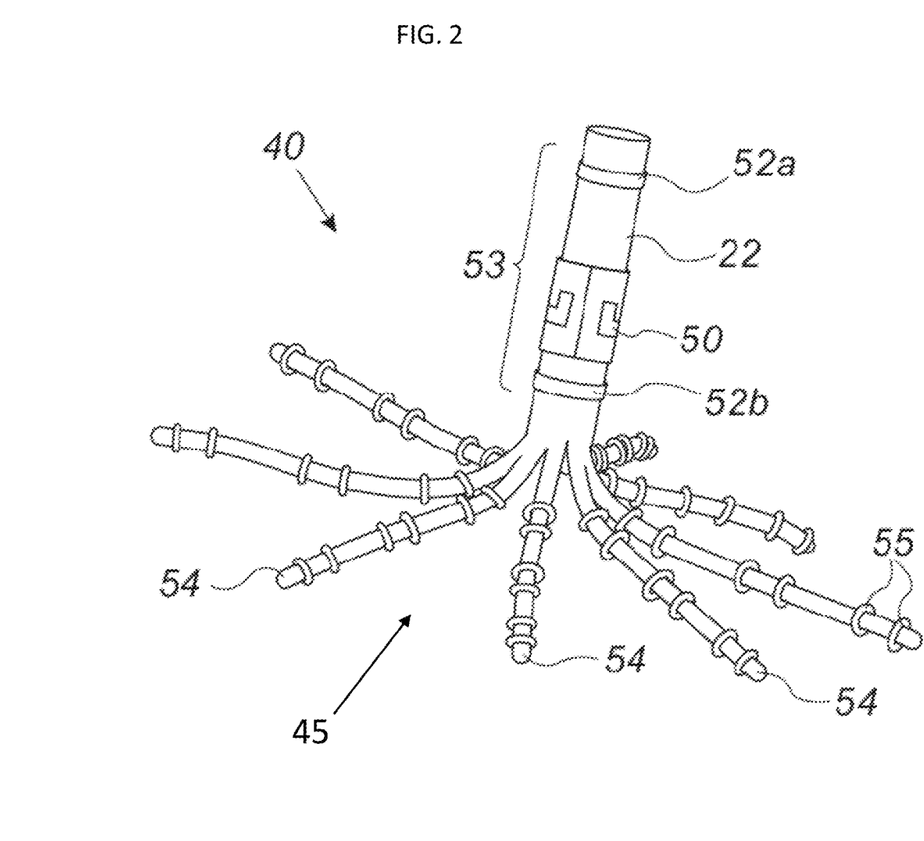
FIG. 2 is a schematic view of a catheter for use in the system of FIG. 1.

Reference is now made to FIG. 1, which is a schematic view of a medical procedure system 20 constructed and operative in accordance with an embodiment of the present invention. Reference is also made to FIG. 2, which is a schematic view of a catheter 40 for use in the system 20 of FIG. 1.

The medical procedure system 20 is used to determine the position of the catheter 40, seen in an inset 25 of FIG. 1 and in more detail in FIG. 2. The catheter 40 includes a shaft 22, a distal portion 45 and catheter electrodes 55 disposed at respective locations on the distal portion 45. The distal portion 45 of the catheter 40 may include a distal end assembly such as a basket or balloon assembly or deflectable arms 54 (as shown in FIG. 2, only some labeled for the sake of simplicity) connected to a distal end of the shaft 22 of the catheter 40. The catheter 40 is configured for inserting into a body-part (e.g., a chamber of a heart 26) of a living subject. The deflectable arms 54 have respective proximal ends connected to the distal end of the shaft 22.

The catheter 40 includes a position sensor 53 disposed on the shaft 22 in a predefined spatial relation to the proximal ends of the deflectable arms 54. The position sensor 53 may include a magnetic sensor 50 and/or at least one shaft electrode 52. The magnetic sensor 50 may include at least one coil, for example, but not limited to, a dual-axis or a triple axis coil arrangement to provide position data for location and orientation including roll. The catheter 40 includes multiple catheter electrodes 55 (only some are labeled in FIG. 2 for the sake of simplicity) disposed at different, respective locations along each of the deflectable arms 54. Typically, the catheter 40 may be used for mapping electrical activity in a heart of the living subject using the electrodes 55, or for performing any other suitable function in a body-part of a living subject. The electrodes 55 are configured to contact tissue of the body-part at respective locations with the body part (e.g., within the chamber of the heart).

The medical procedure system 20 may determine a position and orientation of the shaft 22 of the catheter 40 based on signals provided by the magnetic sensor 50 and/or the shaft electrodes 52 (proximal-electrode 52a and distal-electrode 52b) fitted on the shaft 22, on either side of the magnetic sensor 50. The proximal-electrode 52a, the distal-electrode 52b, the magnetic sensor 50 and at least some of the electrodes 55 are connected by wires running through the shaft 22 via a catheter connector 35 to various driver circuitries in a console 24. In some embodiments, at least two of the electrodes 55 of each of the deflectable arms 54, the shaft electrodes 52, and the magnetic sensor 50 are connected to the driver circuitries in the console 24 via the catheter connector 35. In some embodiments, the distal-electrode 52b and/or the proximal electrode 52a may be omitted.

The illustration shown in FIG. 2 is chosen purely for the sake of conceptual clarity. Other configurations of shaft electrodes 52 and electrodes 55 are possible. Additional functionalities may be included in the position sensor 53. Elements which are not relevant to the disclosed embodiments of the invention, such as irrigation ports, are omitted for the sake of clarity.

A physician 30 navigates the catheter 40 to a target location in a body part (e.g., the heart 26) of a patient 28 by manipulating the shaft 22 using a manipulator 32 near the proximal end of the catheter 40 and/or deflection from a sheath 23. The catheter 40 is inserted through the sheath 23, with the deflectable arms 54 gathered together, and only after the catheter 40 is retracted from the sheath 23, the deflectable arms 54 are able to spread and regain their intended functional shape. By containing deflectable arms 54 together, the sheath 23 also serves to minimize vascular trauma on its way to the target location.

Console 24 comprises processing circuitry 41, typically a general-purpose computer and a suitable front end and interface circuits 44 for generating signals in, and/or receiving signals from, body surface electrodes 49 which are attached by wires running through a cable 39 to the chest and to the back, or any other suitable skin surface, of the patient 28.

Console 24 further comprises a magnetic-sensing subsystem. The patient 28 is placed in a magnetic field generated by a pad containing at least one magnetic field radiator 42, which is driven by a unit 43 disposed in the console 24. The magnetic field radiator(s) 42 is configured to transmit alternating magnetic fields into a region where the body-part (e.g., the heart 26) is located. The magnetic fields generated by the magnetic field radiator(s) 42 generate direction signals in the magnetic sensor 50. The magnetic sensor 50 is configured to detect at least part of the transmitted alternating magnetic fields and provide the direction signals as corresponding electrical inputs to the processing circuitry 41.

In some embodiments, the processing circuitry 41 uses the position-signals received from the shaft electrodes 52, the magnetic sensor 50 and the electrodes 55 to estimate a position of the catheter 40 inside an organ, such as inside a cardiac chamber. In some embodiments, the processing circuitry 41 correlates the position signals received from the electrodes 52, 55 with previously acquired magnetic location-calibrated position signals, to estimate the position of the catheter 40 inside a cardiac chamber. The position coordinates of the shaft electrodes 52 and the electrodes 55 may be determined by the processing circuitry 41 based on, among other inputs, measured impedances, or on proportions of currents distribution, between the electrodes 52, 55 and the body surface electrodes 49. The console 24 drives a display 27, which shows the distal portion of the catheter 40 inside the heart 26.

The method of position sensing using current distribution measurements and/or external magnetic fields is implemented in various medical applications, for example, in the Carto® system, produced by Biosense Webster Inc. (Irvine, Calif.), and is described in detail in U.S. Pat. Nos. 5,391,199, 6,690,963, 6,484,118, 6,239,724, 6,618,612, 6,332,089, 7,756,576, 7,869,865, and 7,848,787, in PCT Patent Publication WO 96/05768, and in U.S. Patent Application Publications 2002/0065455 A1, 2003/0120150 A1 and 2004/0068178 A1.

The Carto®3 system applies an Active Current Location (ACL) impedance-based position-tracking method. In some embodiments, using the ACL method, the processing circuitry 41 is configured to create a mapping (e.g., current-position matrix (CPM)) between indications of electrical impedance and positions in a magnetic coordinate frame of the magnetic field radiator(s) 42. The processing circuitry 41 estimates the positions of the shaft electrodes 52 and the electrodes 55 by performing a lookup in the CPM.

Processing circuitry 41 is typically programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

FIG. 1 shows only elements related to the disclosed techniques, for the sake of simplicity and clarity. The system 20 typically comprises additional modules and elements that are not directly related to the disclosed techniques, and thus are intentionally omitted from FIG. 1 and from the corresponding description.

The catheter 40 described above includes eight deflectable arms 54 with six electrodes per arm 54. Any suitable catheter may be used instead of the catheter 40, for example, a catheter with a different number of flexible arms and/or electrodes per arm, or a different probe shape such as a balloon catheter, a basket catheter, or a lasso catheter, by way of example only.

The medical procedure system 20 may also perform ablation of heart tissue using any suitable catheter, for example using the catheter 40 or a different catheter and any suitable ablation method. The console 24 may include an RF signal generator 34 configured to generate RF power to be applied by an electrode or electrodes of a catheter connected to the console 24, and one or more of the body surface electrodes 49, to ablate a myocardium of the heart 26. The console 24 may include a pump (not shown), which pumps irrigation fluid into an irrigation channel to a distal portion of a catheter performing ablation. The catheter performing the ablation may also include temperature sensors (not shown) which are used to measure a temperature of the myocardium during ablation and regulate an ablation power and/or an irrigation rate of the pumping of the irrigation fluid according to the measured temperature.

Figure 3:
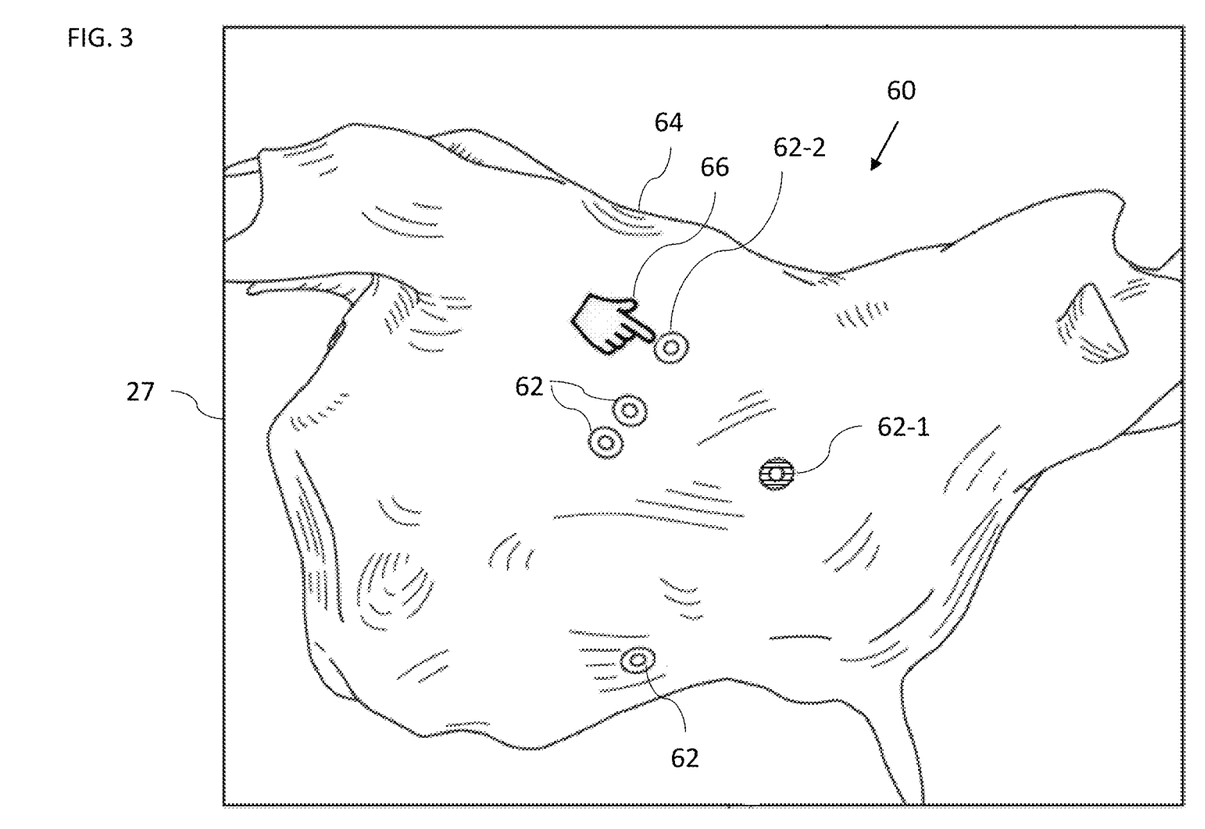
FIG. 3 is a schematic view of a three-dimensional (3D) representation of a chamber of a heart including respective sampling-site markers rendered by the system of FIG. 1.

Reference is now made to FIG. 3, which is a schematic view of a three-dimensional (3D) representation 60 of a chamber of the heart 26 (FIG. 1) including respective sampling-site markers 62 rendered by the system 20 of FIG. 1.

The catheter 40 (FIG. 2) is inserted into the chamber of the heart 26 (FIG. 1) of the living subject and maneuvered among multiple sampling sites to sample electrical activity of tissue of the chamber using respective ones of the catheter electrodes 55 (FIG. 2) at each of the sampling sites. The examples of FIGS. 3-9 are based on using a catheter with five splines, for example, a PENTARAY catheter. Any suitable catheter with more or less than five splines may be used. In some embodiments, any suitable catheter, such as a balloon, basket, or lasso catheter, may be used. The sampling time at each sampling site may be any suitable duration, for example, in a range between 20-30 seconds. In other embodiments the sampling time may be less than 20 seconds or more than 30 seconds.

The processing circuitry 41 (FIG. 1) receives signals provided by the catheter 40 (FIG. 2), and in response to the signals, computes, for each sampling site, a sampling position of the catheter 40 and respective electrode positions of the respective catheter electrodes 55 (FIG. 2). The sampling position of the catheter 40 may be any suitable position of the catheter 40, for example, a distal end of the shaft 22 (FIG. 2) of the catheter 40, or a position of a position sensor (such as the magnetic sensor 50 (FIG. 2)) on the shaft 22, or an average position of the electrodes 55 at the sampling site. The computed positions are generally projected on to a surface 64 representing the surface of the chamber of the heart. The surface 64 representing the chamber may be acquired from a previous scan, such as a CT or MRI, which is registered with the system 20. The signals may be provided by electrodes 55 and/or other position sensor(s) or transducer(s) of the catheter 40. The signals may be received by the processing circuitry 41 from the catheter 40 via a cable or wirelessly. Additionally, or alternatively, the processing circuitry 41 may receive the signals from body surface electrodes 49 which sense the signals emitted by the catheter 40.

In some embodiments, the processing circuitry 41 (FIG. 1) is configured to compute, for each sampling site, the sampling position and the electrode positions as average positions of the catheter 40 (FIG. 2) and the catheter electrodes 55 (FIG. 2), respectively, averaged over the sampling time of that sampling site.

The processing circuitry 41 (FIG. 1) identifies electrical activity of the tissue sensed by the catheter electrodes 55 (FIG. 2) sampled at respective sampling sites based on the received signals. Identifying electrical activity may include identifying intensity of electrical activity (e.g., based on a magnitude of the signals), and/or regions of interest such as focal activity or rotational activity, by way of example only. Focal activity may be indicated by a repetitive activation pattern that demonstrates early consecutive QS morphology. US Patent Publication 2017/0202470 of Urman et al., describes a system and method of identifying focal sources. Any suitable method to identify focal sources may be used. Rotational activity may be indicated by a repetitive activation pattern which demonstrates rotation activity. US Patent Publication 2017/0202515 of Ben Zrihem et al., describes a method of atrial rotational activity pattern (RAP) source detection which includes detecting, via a plurality of sensors, electro-cardiogram (ECG) signals over time, each ECG signal detected via one of the plurality of sensors and indicating electrical activity of a heart. Any suitable method to identify rotational activity may be used.

The processing circuitry 41 (FIG. 1) renders to the display 27 (FIG. 1) the 3D representation 60 of the chamber including respective sampling-site markers 62 indicating the computed sampling position of the catheter 40 (FIG. 2) at respective sampling sites. As previously mentioned, the computed sampling positions are projected on to the surface 64 of the chamber. Each sampling-site marker 62 is represented by two concentric circles in FIG. 3. The sampling-site markers 62 may be represented using any suitable symbol or shape, for example, a circle or a square or a triangle.

In some embodiments, a sampling site that is deemed to be unstable due to catheter movement exceeding a threshold during the sampling time may be formatted and/or presented differently from the other sampling-site markers 62. In the example of FIG. 3, an unstable sampling site is indicated using stripes in the sampling-site marker 62-1. The threshold may be any suitable value, for example, but not limited to, in the range of 0.5 mm to 10 mm.

FIG. 3 also shows a user cursor 66 hovering over the sampling-site marker 62-2 prior to selection of the sampling-site marker 62-2. In some embodiments, the sampling-site marker 62-2 may be selected by touching a touch-sensitive screen.

Figure 4:
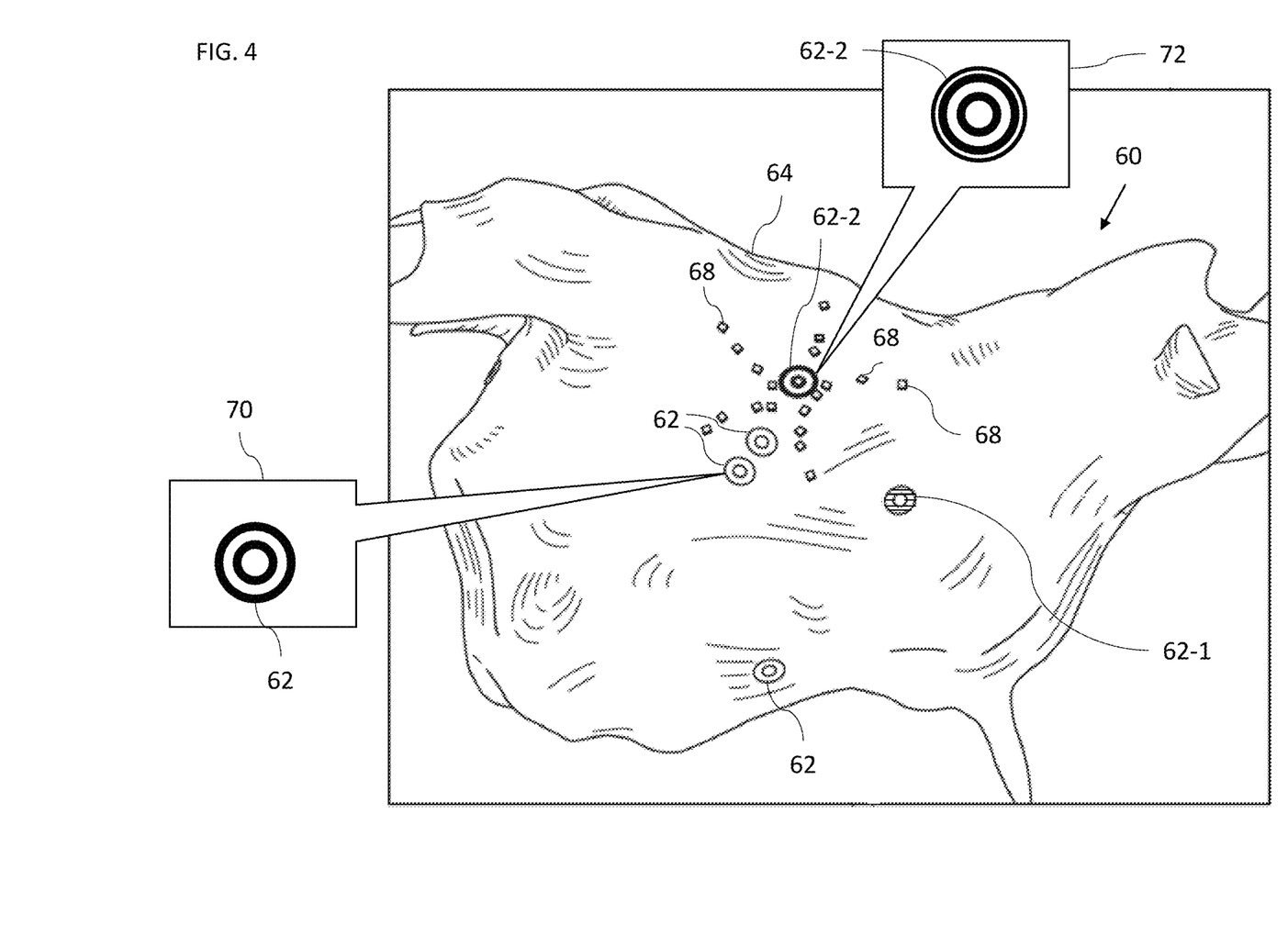
FIG. 4 is a schematic view of the 3D representation illustrating selection of one of the sampling-site markers of FIG. 3.

Reference is now made to FIG. 4, which is a schematic view of the 3D representation 60 illustrating selection of the sampling-site marker 62-2 of FIG. 3. The processing circuitry 41 (FIG. 1) receives user input selecting the sampling-site marker 62-2. The processing circuitry 41 updates the rendered 3D representation 60, responsively to the received user input, to include electrode markers 68 (only some labeled for the sake of simplicity) indicating the respective (projected) electrode positions of the respective catheter electrodes 55 (projected onto the surface 64) while the catheter 40 (FIG. 2) was sampling the electrical activity of the tissue at the sampling site corresponding to the selected sampling-site marker 62-2. FIG. 4 shows that the electrode markers 68 are arranged in five lines which diverge from the sampling-site marker 62-2. The five lines correspond to the five splines of the catheter 40, which in this example is a PENTARAY catheter. In other embodiments, any suitable catheter may be used.

Each electrode marker 68 is represented by a square. The electrode markers 68 may be represented using any suitable symbol or shape, for example, a circle or a triangle.

Upon selection of the sampling-site marker 62-2, the processing circuitry 41 updates the rendered 3D representation 60 to highlight the selected sampling-site marker 62-2, e.g., by surrounding it with another circle. Additionally, or alternatively, the sampling-site marker 62-2 may be highlighted by increasing a brightness, and/or changing a color, of the sampling-site marker 62-2. The inset 70 shows one of the sampling-site markers 62, which has not been selected and is therefore not highlighted. The inset 72 shows the sampling-site marker 62-2 highlighted after selection.

Figure 5:
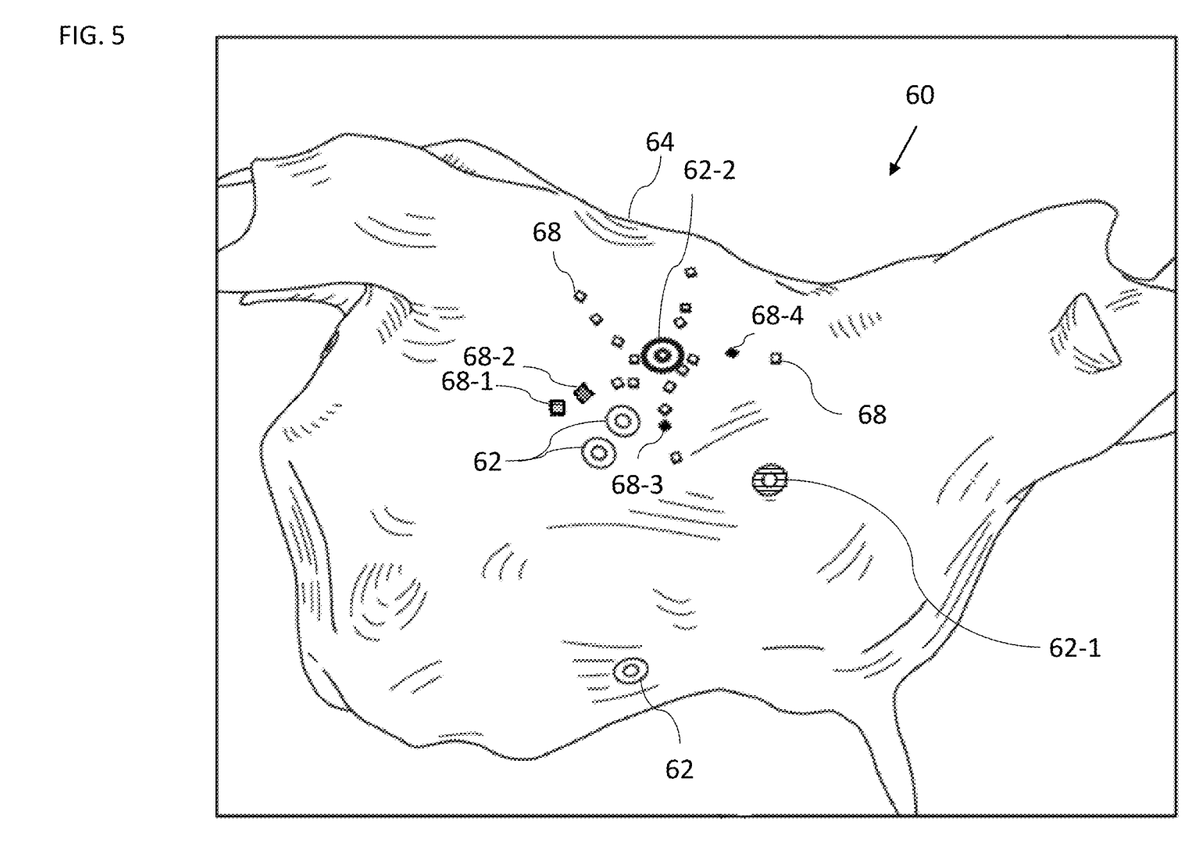
FIG. 5 is a schematic view of the 3D representation illustrating selection of one of the sampling-site markers of FIG. 3 in accordance with an alternative embodiment.

Reference is now made to FIG. 5, which is a schematic view of the 3D representation 60 illustrating selection of the sampling-site marker 62-2 of FIG. 3 in accordance with an alternative embodiment. Some of the electrode markers 68-1, 68-2, 68-3, 68-4 in FIG. 5 are presented differently (e.g., enlarged and/or colored and/or shaded differently) than other electrode markers 68. In particular, the electrode markers 68-1, 68-2 are represented as larger squares than the squares of the other electrode markers 68, while the electrode markers 68-3, 68-4 are formatted with a black filler. The electrode markers 68-1, 68-2 may represent a region of interest of electrical activity, such as focal activity or rotational activity of the tissue sensed by the respective electrodes 55 (FIG. 2). Additionally, electrode marker 68-1 has a lighter filler color than electrode marker 68-2 indicating that the electrical activity associated with electrode marker 68-1 has a lower intensity than the electrical activity associated with the electrode marker 68-2. The electrode markers 68-3, 68-4 may represent electrical activity below a threshold as sensed by the respective electrodes 55. The electrical activity associated with the electrode markers 68-3, 68-4 may be excluded from certain calculations, for example, calculations to determine a region of interest such as focal activity and/or rotational activity.

The processing circuitry 41 may update the rendered 3D representation 60, responsively to the received user input, to include the electrode markers 68 with at least one of the electrode markers 68-1, 68-2, 68-3, 68-4 having a different presentation type than other ones of the electrode markers 68 responsively to the identified electrical activity of the tissue sensed by respective catheter electrodes (corresponding with the markers 68-1, 68-2, 68-3, 68-4). The identified electrical activity may be associated with any one or more of the following: electrical activity below a threshold activity level, focal activity, and/or rotational activity. The different presentation type(s) may include using: a larger electrode marker 68 compared with the other electrode markers 68; and/or a different color electrode marker 68 compared with the other electrode markers 68; and/or different shapes, shading, patterns and/or brightness, by way of example only.

The processing circuitry 41 may format the electrode marker(s) 68-1, 68-2, 68-3, 68-4 according to an intensity of the identified electrical activity of the tissue sensed by the respective catheter electrodes 55 (FIG. 2). The format may include a color, shading, pattern, and/or brightness, by way of example.

In all the embodiments described herein, the various markers may optionally be displayed over other mapping schemes for example, maps colored according to local activation time (LAT) or bipolar voltages.

Figure 6:
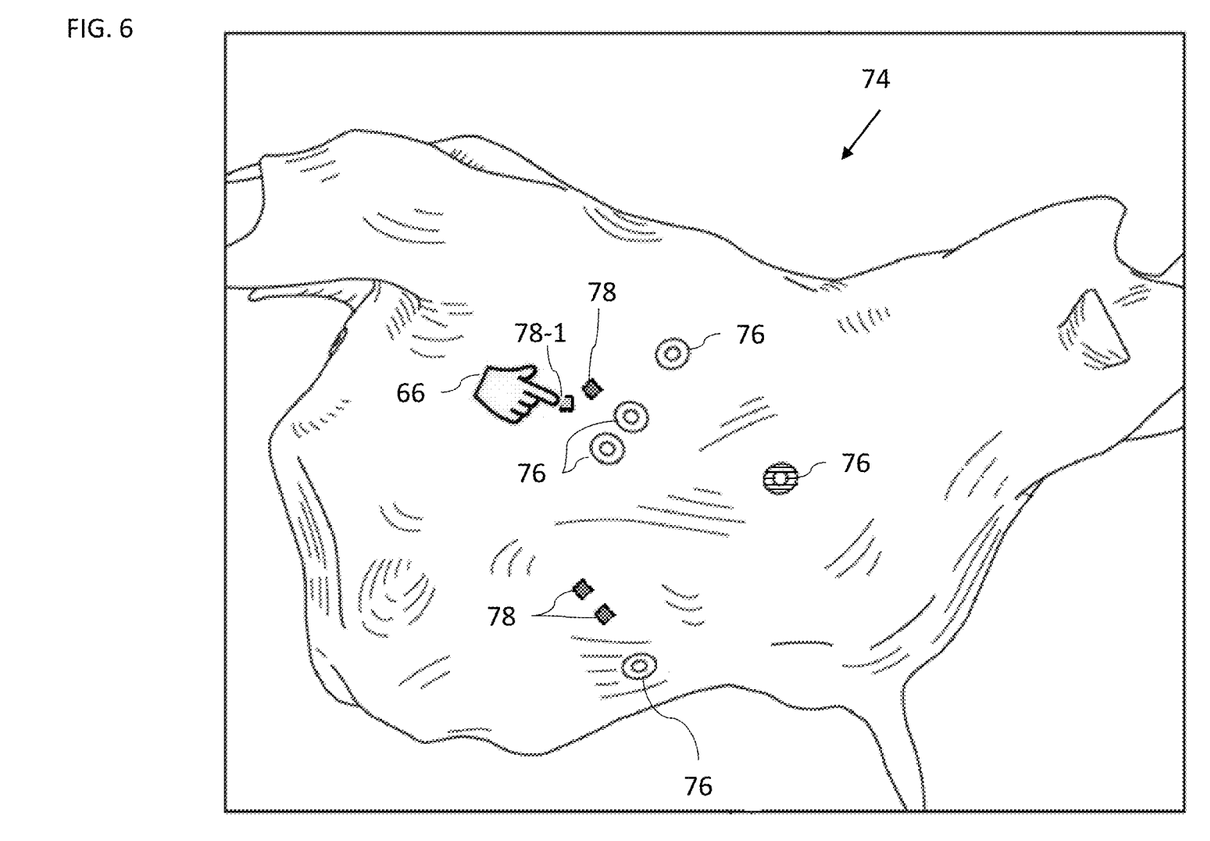
FIG. 6 is a schematic view of a three-dimensional (3D) representation of a chamber of a heart including respective sampling-site markers and electrode markers rendered by the system of FIG. 1 in accordance with an alternative embodiment.

Reference is now made to FIG. 6, which is a schematic view of a three-dimensional (3D) representation 74 of a chamber of a heart including respective sampling-site markers 76 and electrode markers 78 rendered by the system 20 of FIG. 1 in accordance with an alternative embodiment. FIG. 6 shows the electrode markers 78 associated with the sampling-site markers 76 even when none of the sampling-site markers 76 have been selected by a user. The electrode markers 78 may be associated with a region of interest such as focal activity or rotational activity. FIG. 6 also shows the user cursor 66 hovering over the electrode marker 78-1 prior to selection of the electrode marker 78-1.

Figure 7:
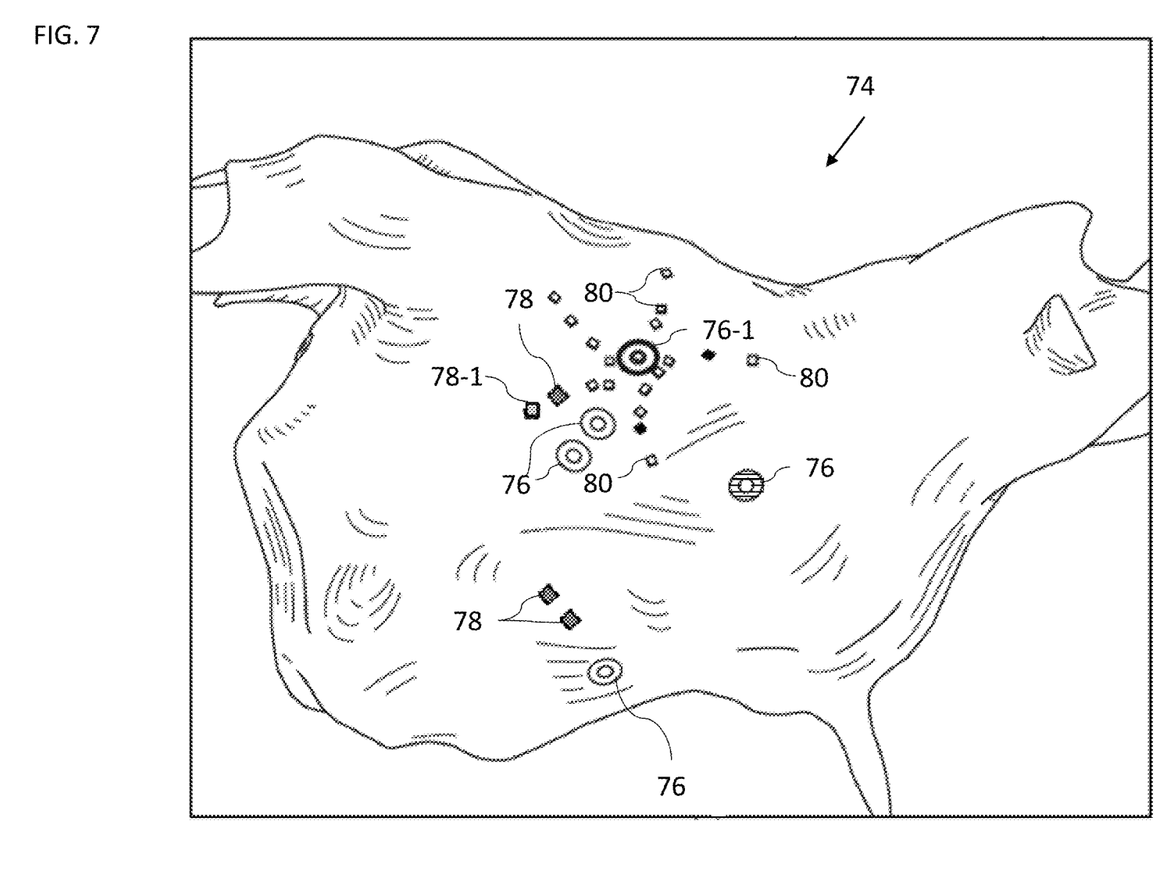
FIG. 7 is a schematic view of the 3D representation illustrating selection of one of the electrode markers of FIG. 6.

Reference is now made to FIG. 7, which is a schematic view of the 3D representation 74 illustrating selection of the electrode marker 78-1 of FIG. 6. Selecting the electrode marker 78-1 results in updating the 3D representation 74 to show other electrode markers 80 (only some labeled for the sake of simplicity) associated with the sampling-site marker 76-1 to which the electrode marker 78-1 is associated. Similarly selecting any of the electrode markers 78 results in updating the 3D representation 74 to show the electrode markers 80 associated with the sampling-site marker 76 to which the selected electrode marker 78 is associated. Additionally, selecting the sampling-site marker 76-1 results in showing the electrode markers 80 associated with the sampling-site marker 76-1.

Figure 8:
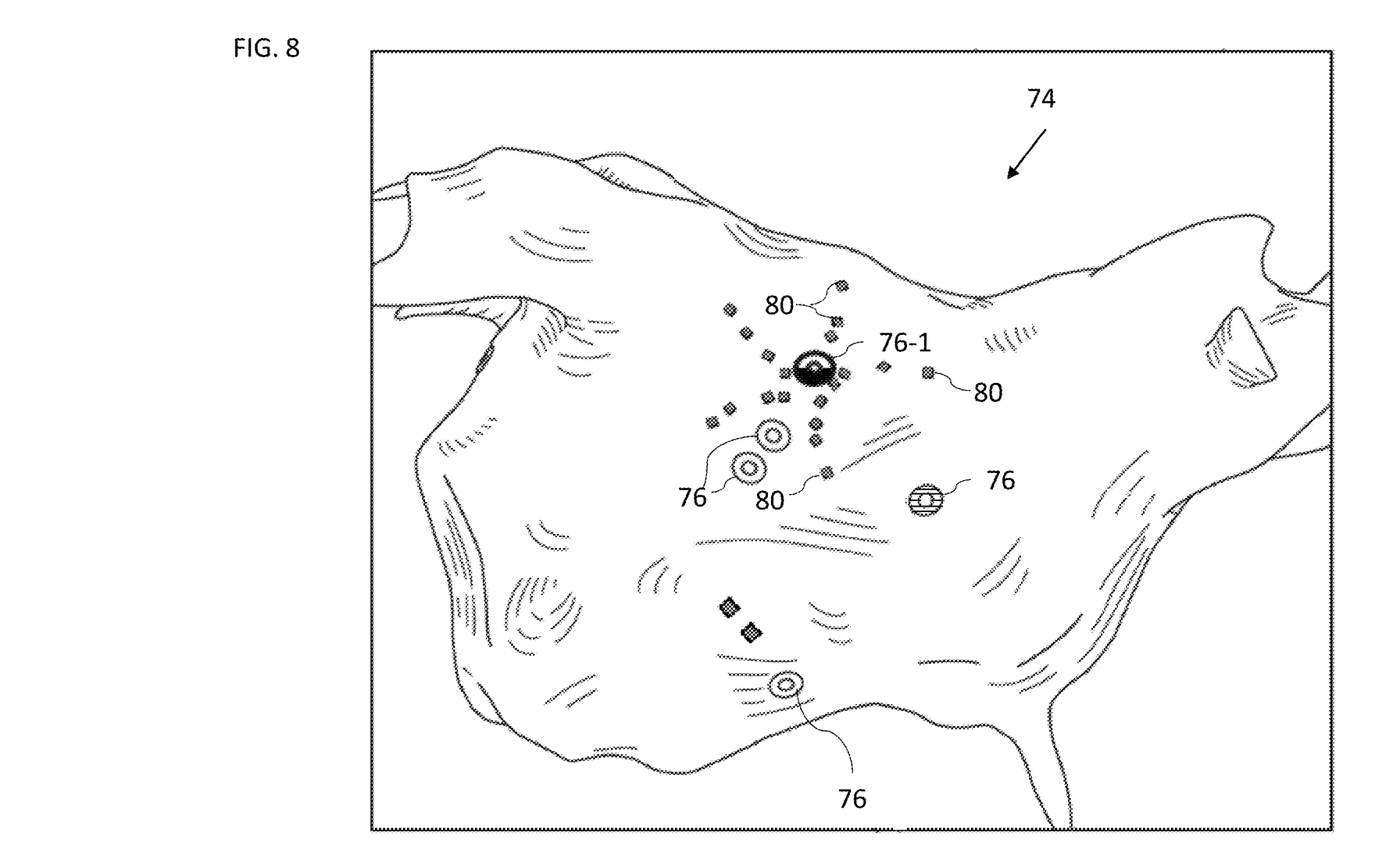
FIG. 8 is a schematic view of the 3D representation of FIG. 7 during a recalculation.

Reference is now made to FIG. 8, which is a schematic view of the 3D representation 74 of FIG. 7 during a recalculation. The user may select to perform a recalculation to identify electrical activity, such as regions of interest, of the tissue sensed by the electrodes 55 for any one of the sampling sites associated with one of the sampling-site markers 76. The recalculation may be performed, for example, after the user excludes or includes the sensed electrical activity of the tissue sensed by one or more of the electrodes 55 at one of the sampling sites. The user may exclude or include the sensed electrical activity of the tissue sensed by one or more of the electrodes 55 via selection of the associated electrode marker(s) 80, for example, by right-clicking with a mouse on the electrode marker(s) 80 and selecting a recalculation from a list in a pop-up window, for example, or using any other suitable selection method. The recalculation may be triggered by selecting the associated sampling-site marker 76, for example, by right-clicking with a mouse on the sampling-site marker 76 and selecting a recalculation from a list in a pop-up window, for example, or using any other suitable selection method. During recalculation, the electrode markers 80 may be shown with a different presentation, for example, with a gray filler, and the selected sampling-site marker 76-1 may show the progress of the recalculation using a black filler which increases as the recalculation progresses.

Figure 9:
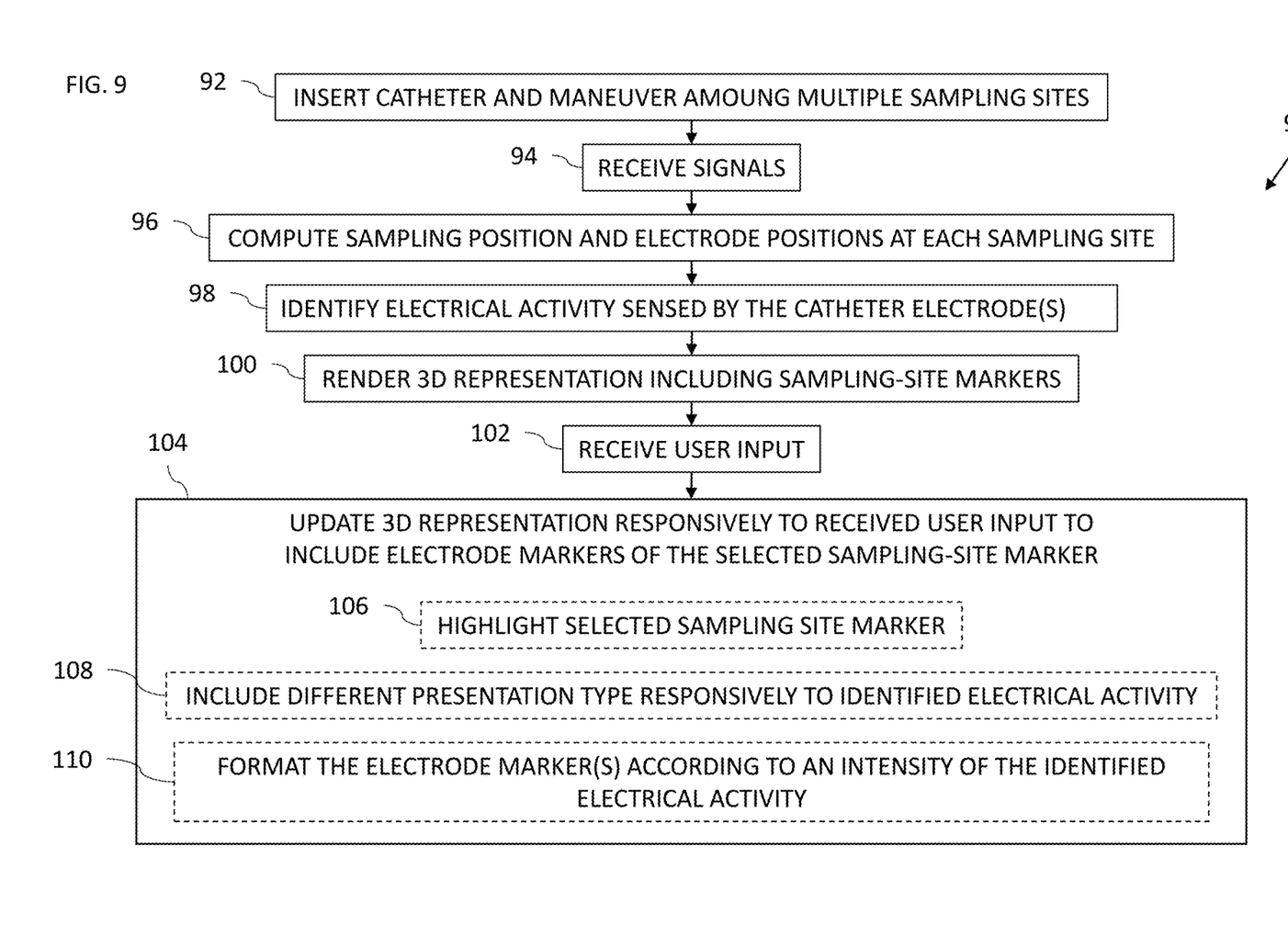
FIG. 9 is a flowchart including steps in a method of operation of the system of FIG. 1.

Reference is now made to FIG. 9, which is a flowchart 90 including steps in a method of operation of the system 20 of FIG. 1.

The catheter 40 (FIG. 2) is configured to be inserted (block 92) into the chamber of the heart 26 (FIG. 1) of a living subject and maneuvered among multiple sampling sites to sample electrical activity of tissue of the chamber using respective ones of the catheter electrodes 55 (FIG. 2) at each sampling site.

The processing circuitry 41 (FIG. 1) is configured to receive (block 94) signals provided by the catheter 40 (FIG. 2), and in response to the signals, compute (block 96), for each sampling site, the sampling position of the catheter 40 and respective electrode positions of the respective ones of the catheter electrodes 55 (FIG. 2). In some embodiments, the processing circuitry 41 is configured to compute, for each sampling site, the sampling position and the electrode positions as average positions of the catheter 40 and the catheter electrodes 55, respectively, averaged over the sampling time of that sampling site.

The processing circuitry 41 (FIG. 1) is configured to identify (block 98) electrical activity of the tissue sensed by respective ones of the catheter electrodes 55 sampled at respective sampling sites. The processing circuitry 41 is configured to render (block 100) to the display the 3D representation 60 (FIG. 4), 74 (FIG. 7) of the chamber including respective sampling-site markers 62 (FIG. 4), 76 (FIG. 7) indicating the computed sampling position of the catheter 40 at respective sampling sites. The processing circuitry 41 is configured to receive (block 102) a user input selecting one of the sampling-site markers 62, 76.

The processing circuitry 41 (FIG. 1) is configured to update (block 104) the rendered 3D representation 60, 74, responsively to the received user input, to include electrode markers 68 (FIG. 4), 80 (FIG. 7) indicating the respective electrode positions of the respective catheter electrodes 55 (FIG. 2) while the catheter 40 (FIG. 2) was sampling the electrical activity of the tissue at a respective one of the sampling sites corresponding to the selected sampling-site marker 62, 76. In some embodiments, the processing circuitry 41 (FIG. 1) is configured to update the rendered 3D representation 60, 74 to highlight (block 106) the selected sampling-site marker 62, 76.

The processing circuitry 41 (FIG. 1) is configured to update the rendered 3D representation 60, 74, responsively to the received user input, to include (block 108) the electrode markers 68, 80 with at least one of the electrode markers 68, 80 having a different presentation type than other ones of the electrode markers 68, 80 responsively to the identified electrical activity of the tissue sensed by at least one respective one of catheter electrodes 55. The identified electrical activity may include electrical activity below a threshold activity level, and/or focal activity, and/or rotational activity. The different presentation type may include using: a larger electrode marker compared with the other electrode markers; and/or a different color electrode marker compared with the other electrode markers; and/or different shapes, shading, patterns and/or brightness, by way of example.

The processing circuitry 41 (FIG. 1) is configured to format (block 110) any of the electrode marker 68, 80 according to an intensity of the identified electrical activity of the tissue sensed by the respective catheter electrodes 55. The format may include a color, shading, pattern, and/or brightness, by way of example.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 99%.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The embodiments described above are cited by way of example, and the present invention is not limited by what has been particularly shown and described hereinabove. Rather the scope of the invention includes both combinations and subcombinations of the various features described hereinabove, as well as variations and modifications thereof which would occur to persons skilled in the art upon reading the foregoing description and which are not disclosed in the prior art.

What is claimed is:

1. A medical system, comprising:
a catheter including a distal portion and catheter electrodes disposed at respective locations on the distal portion, and configured to be inserted into a chamber of a heart of a living subject and maneuvered among multiple sampling sites to sample electrical activity of tissue of the chamber with the catheter electrodes;
a display; and
processing circuitry configured to:
receive signals provided by the catheter, and in response to the signals, compute, for each of the sampling sites, a sampling position of the catheter and respective electrode positions of each of the catheter electrodes at that sampling position of the catheter;
render to the display a three-dimensional (3D) representation of the chamber including sampling-site markers indicating the computed sampling position of the catheter at each of the sampling sites without including electrode markers indicating the computed electrode positions, wherein each of the sampling site markers and each of the electrode markers are annotations included on the rendered 3D representation of the chamber;
receive a user input selecting one of the sampling-site markers; and
update the rendered 3D representation, responsively to the received user input, to selectively display all the electrode markers associated with the selected sampling-site marker, wherein the electrode markers associated with the selected sampling-site marker indicate positions of each the catheter electrodes while the catheter was at a sampling site associated with the user selected sampling-site marker.

2. The system according to claim 1, wherein the processing circuitry is configured to compute, for each of the sampling sites, the sampling position and the electrode positions as average positions of the catheter and the catheter electrodes, respectively, averaged over a sampling time.

3. The system according to claim 1, wherein the processing circuitry is configured to update the rendered 3D representation to highlight the selected sampling-site marker.

4. The system according to claim 1, wherein the processing circuitry is configured to:
identify electrical activity of the tissue sensed by the catheter electrodes at respective sampling sites; and
update the rendered 3D representation, responsively to the received user input, to include the electrode markers with at least one of the electrode markers having a different presentation type than other ones of the electrode markers responsively to the identified electrical activity of the tissue sensed by at least one of the catheter electrodes.

5. The system according to claim 4, wherein the identified electrical activity is activity selected from a group including: electrical activity below a threshold activity level, focal activity, and rotational activity.

6. The system according to claim 4, wherein the different presentation type is selected from a group that includes using a larger electrode marker compared with the other electrode markers and using a different color electrode marker compared with the other electrode markers.

7. The system according to claim 4, wherein the processing circuitry is configured to format the at least one electrode marker according to an intensity of the identified electrical activity of the tissue sensed by the at least one of the catheter electrodes.

8. The medical system according to claim 1, wherein the sampling position of the catheter is a sensed position of a position sensor or a transducer disposed on the shaft of the catheter.

9. The medical system according to claim 1, wherein the sampling position of the catheter is an average position of the catheter electrodes that are disposed on the distal portion.

10. A medical method, comprising:
receiving signals provided by a catheter, the catheter including a distal portion and catheter electrodes disposed at respective locations on the distal portion, and configured to be inserted into a chamber of a heart of a living subject and maneuvered among multiple sampling sites to sample electrical activity of tissue of the chamber with the catheter electrodes;
in response to the signals, computing, for each of the sampling sites, a sampling position of the catheter and respective electrode positions of each of the catheter electrodes at that sampling position of the catheter;
rendering to a display a three-dimensional (3D) representation of the chamber including sampling-site markers indicating the computed sampling position of the catheter at each of the sampling sites without including electrode markers indicating the computed electrode positions, wherein each of the sampling site markers and the electrode markers are annotations included on the rendered 3D representation of the chamber;
receiving a user input selecting one of the sampling-site markers; and
updating the rendered 3D representation, responsively to the received user input, to selectively display all the electrode markers associated with the selected sampling-site marker, wherein the electrode markers associated with the selected sampling-site marker indicate positions of each the catheter electrodes while the catheter was at a sampling site associated with the user selected sampling-site marker.

11. The method according to claim 10, wherein the computing includes computing, for each of the sampling sites, the sampling position and the electrode positions as average positions of the catheter and the catheter electrodes, respectively, averaged over a sampling time.

12. The method according to claim 10, wherein the updating includes updating the rendered 3D representation to highlight the selected sampling-site marker.

13. The method according to claim 10, further comprising identifying electrical activity of the tissue sensed by the catheter electrodes at the respective sampling sites, wherein the updating includes updating the rendered 3D representation, responsively to the received user input, to include the electrode markers with at least one of the electrode markers having a different presentation type than other ones of the electrode markers responsively to the identified electrical activity of the tissue sensed by at least one of the catheter electrodes.

14. The method according to claim 13, wherein the identified electrical activity is activity selected from a group including: electrical activity below a threshold activity level, focal activity, and rotational activity.

15. The method according to claim 13, wherein the different presentation type is selected from a group that includes using a larger electrode marker compared with the other electrode markers and using a different color electrode marker compared with the other electrode markers.

16. The method according to claim 13, further comprising formatting the at least one electrode marker according to an intensity of the identified electrical activity of the tissue sensed by the at least one respective one of the catheter electrodes.

17. The method according to claim 10, wherein the sampling position of the catheter is defined based on an average position of the catheter electrodes that are disposed on the distal portion.

18. The method according to claim 10, wherein the sampling position of the catheter is defined as a sensed position of a position sensor or a transducer disposed on the shaft of the catheter.

19. A software product, comprising a non-transient computer-readable medium in which program instructions are stored, which instructions, when read by a central processing unit (CPU), cause the CPU to:

receive signals provided by a catheter, the catheter including a distal portion and catheter electrodes disposed at respective locations on the distal portion, and configured to be inserted into a chamber of a heart of a living subject and maneuvered among multiple sampling sites to sample electrical activity of tissue of the chamber with the catheter electrodes at each of the sampling sites;

compute, in response to the signals, for each of the sampling sites, a sampling position of the catheter and respective electrode positions of each of the catheter electrodes at that sampling position of the catheter;

render to a display a three-dimensional (3D) representation of the chamber including sampling-site markers indicating the computed sampling position of the catheter at each of the sampling sites, without including electrode markers indicating the computed electrode positions, wherein each of the sampling site markers and each of the electrode markers are annotations included on the rendered 3D representation of the chamber;

receive a user input selecting one of the sampling-site markers; and update the rendered 3D representation, responsively to the received user input, to selectively display all the electrode markers associated with the selected sampling-site marker, wherein the electrode markers associated with the selected sampling-site marker indicate positions of each the catheter electrodes while the catheter was at a sampling site associated with the user selected sampling-site marker.

20. The software product on non-transient computer-readable medium according to claim 19, wherein the sampling position of the catheter is defined as a sensed position of a position sensor or a transducer disposed on the shaft of the catheter.

21. The software product on non-transient computer readable medium according to claim 19, wherein the sampling position of the catheter is defined based on an average position of the catheter electrodes that are disposed on the distal portion.

* * * * *